United States Patent [19]

Ratcliff

[11] Patent Number: 4,786,492

[45] Date of Patent: * Nov. 22, 1988

[54] METHOD AND COMPOSITION FOR PREVENTION AND TREATMENT OF ORAL DISEASE

[76] Inventor: Perry A. Ratcliff, 7125 E. Lincoln Dr., Scottsdale, Ariz. 85253

[*] Notice: The portion of the term of this patent subsequent to Aug. 25, 2004 has been disclaimed.

[21] Appl. No.: 76,379

[22] Filed: Jul. 22, 1987

Related U.S. Application Data

[63] Continuation of Ser. No. 17,241, Dec. 29, 1986, Pat. No. 4,696,811.

[51] Int. Cl.$^4$ .................. A61K 7/20; A61K 33/20
[52] U.S. Cl. ............................ 424/53; 424/149
[58] Field of Search ........................ 424/53, 149

[56] References Cited

U.S. PATENT DOCUMENTS

| | | | |
|---|---|---|---|
| 2,451,897 | 10/1948 | Woodward | 99/111 |
| 2,482,958 | 9/1949 | Woodward | 99/150 |
| 2,546,258 | 3/1951 | Taylor | 99/150 |
| 2,711,363 | 6/1955 | Waihel | 2/85 |
| 2,871,097 | 1/1959 | Rapson | 23/152 |
| 3,084,995 | 4/1963 | Grubitsch | 23/152 |
| 3,147,124 | 9/1964 | Wentworth | 99/116 |
| 3,322,497 | 5/1967 | Martin | 23/152 |
| 3,585,147 | 6/1971 | Gordon | 252/187 |
| 3,591,515 | 7/1971 | Lovely et al. | 252/187 |
| 3,593,494 | 7/1971 | Durrell et al. | 23/154 |
| 3,754,079 | 8/1973 | Callerame | 423/472 |
| 3,828,097 | 8/1974 | Callerame | 23/72 |
| 4,104,190 | 8/1978 | Hartshorn | 252/187 |
| 4,247,531 | 1/1981 | Hicks | 423/477 |
| 4,250,144 | 2/1981 | Ratigan | 422/112 |
| 4,250,159 | 2/1981 | Cowley | 23/230 |
| 4,292,292 | 9/1981 | Hicks et al. | 423/477 |
| 4,330,531 | 5/1982 | Alliger | 424/53 |
| 4,362,707 | 12/1982 | Hardee et al. | 423/478 |
| 4,381,290 | 4/1983 | Hardee et al. | 423/478 |
| 4,396,592 | 8/1983 | Combroux | 423/478 |
| 4,414,193 | 11/1983 | Fredette et al. | 423/478 |
| 4,689,215 | 8/1987 | Ratcliff | 424/53 |
| 4,696,811 | 9/1987 | Ratcliff | 424/53 |

*Primary Examiner*—Shep K. Rose
*Attorney, Agent, or Firm*—Cahill, Sutton & Thomas

[57] ABSTRACT

The use of stabilized chlorine dioxide as a composition for the treatment and prevention of oral disease and the reduction of oral malodor is disclosed. Chlorine dioxide is an effective anti-plaque agent, anti-gingivitis and anti-periodontitis agent, and also effective to destroy malodorous sulfur compounds. Preferred concentrations are in the range of 0.005% to 2% and the chlorine dioxide may be in the form of a wash or rinse in solution, a soak or as a toothpaste.

4 Claims, No Drawings

METHOD AND COMPOSITION FOR PREVENTION AND TREATMENT OF ORAL DISEASE

This is a continuation of application Ser. No. 017,241, filed Dec. 29, 1986, now U.S. Pat. No. 4,696,811.

The present invention relates to a method and composition for the prevention and treatment of oral disease and reduction of mouth odors. More particularly, the present invention relates to the use of stabilized chlorine dioxide for the prevention and treatment of oral disease and reduction of mouth odors.

The volatile sulfur compounds, hydrogen sulfide ($H_2S$)methylmercaptan ($CH_3SH$) and di-methylmercaptan ($CH_3)_2S$ are recognized in the current dental literature as being the major contributors to oral malodor. Numerous researchers using organoleptic, chemical, amperometric, mass spectrometric, or gas liquid chromatographic methods have demonstrated that these volatile sulfur compounds are present in the head space and vapor of putrified saliva and in individual samples of mouth air. In most persons, hydrogen sulfide and methylmercaptan constitute over 90% of the total volatile sulfur content identified in mouth air.

These malodorous volatile sulfur compounds are generated primarily through the putrifactive action of oral microorganisms on sulfur containing amino acids, peptones or proteins found in the mouth. These substrates are readily available in saliva and dental plaque or may be derived from proteinaceous food particles trapped between the teeth, in the gingival crevice or adhering to the mucous membranes and the irregular surface of the tongue as well as exroliated oral epithelium, food debris and the like. Current studies have indicated that mouth odor not only comes from the posterior dorsal surface of the tongue but also from periodontal pockets. People with periodontal involvement have an attendant increase in oral malodor from disintegrated epithelial cells.

It is commonly accepted that the etiology of both smooth surface dental caries and periodontal disease is directly associated with the accumulation on teeth of bacterial plaque. Dental plaque is formed by a combination of events starting with a salivary proteanaceous coating of the tooth and the subsequent adhesion to the coating (pellicle) by streptococcus forms. Dextrans produced by bacteria, principally *S. mutans* and *S. sanguis*, are produced from sucrose and with the assistance of bacterially produced glucosyltransferases convert sucrose into glucose and fructose and ultimately the glucose into dextrans. The dextrans act as a nutrient substrate for the growth of additional organisms and the production of acids which demineralize both enamel and dentin causing decay. Other strains of alpha streptococci and lactobacillus organisms include but are not limited to *S. sanguis, S. mitis* and *S. salivarius*.

Gingivitis, adult and juvenile forms of periodontists and acute necrotizing ulerative gingivitis and other periodotopathies are known to be caused by bacteria. Gingivitis occurs from coronol dental plaque and periodontitis by the infection extending into the periodental pocket or space between the gingiva and the tooth root.

Various substances have been tested for their ability to disrupt plaque or prevent its formation and to treat mouth odor such as antibiotics, chlorhexdines, oxine, and alexidine.

The prior art compositions that have been used and tested have found some acceptance but are generally of limited efficacy in reducing or preventing dental caries and periodontitis, gingivitis, plaque accumulation and mouth malodor. Accordingly, there exists a clear need for a composition which will effectively inhibit or control the formation of bacterial plaque and suppress organisms such as but not limited to (1) *S. mutans*, which is implicated as the major cause of human dental decay; (2) *Bacteroides gingivalis*, an *Actinobacillus actinomycetumcomitans* which is implicated in human periodontitis; and (3) will reduce odor intensity in the mouth through the control of hydrogen sulfide and methylmercaptan.

Broadly, the present invention contemplates the use of stabilized chlorine dioxide for the treatment of the mouth as a deodorizing agent, anti-plaque agent, bacteriacide for treatment of gingivitis and as a bactericidal fungicidal and viralcidal agent in other related applications. Chlorine dioxide is quite soluble and is widely used as an industrial purification and oxidizing agent in such areas as manufacture of wood pulp, water treatment and similar applications due to its bactericidal, disinfectant, and sterilization qualities. In the present invention a composition containing stabilized chlorine dioxide may be used for treatment of the mouth either in a solution, for example, as a mouthwash or in a toothpaste generally in concentrations of below approximately 0.2% for the control of odorgenic microorganisms, bacterial plaque, gingivitis and bacteria which cause these conditions. Similarly, chlorine dioxide is also effective as a cellular debridement agent following surgical procedures, sanitizer denture soak and contact lens soaking agent.

The use of chlorine dioxide and its effects on man has been clinically evaluated. The relative safety of oral injestion of chlorine dioxide was demonstrated extensively in animals and later in humans by Lubbers, Chauan, and Bianchine, *Environmental Health Perspectives*, Volume 46, Pages 57-62, 1982.

EXAMPLE I

Deodorizing Mouthwash

In an effort to find a suitable control agent for mouth odor, attention was directed towards the use of chlorine dioxide. The characteristics of chlorine dioxide which make it especially useful is that it is antiseptic, a bactericide, generally colorless, odorless, highly stable and has no apparent detrimental or deliterious effect on humans at concentrations involved. As pointed out above, mouth malodor is primarily caused by volatile sulfur compounds, hydrogen sulfide methylmercaptan and dimethyl mercaptan. These chemicals are produced as degradation products of microorganisms acting on exogenous and endogenous proteinaceous substrates, oral epithelium, food debris and saliva. In order to control mouth odor, a deodorizing mouth wash consisting of a solution of 0.02% chlorine dioxide in deionized water was utilized as a rinse. Evidence indicates efficacy at lesser dilutions to 0.005% with more rapid effect at dilutions to 0.2%. Sulfides are readily oxidized by chlorine dioxide. Bacteria implicated in the production of malodor were also effectively controlled. Inhibition of these microorganisms will reduce dental plaque.

The chlorine dioxide mouthwash or rinse solution serves to attack production and origin of malodor from the mouth by splitting the sulfide bonds of both hydrogen sulfide and methylmercaptan. Therefore, delivery of stabilized chlorine dioxide provides reduction and elimination of these odors. Further, the bacteriostatic, bactericidal, fungistatic and fungicidal activity of stabilized chlorine dioxide will reduce the number of microorganisms which assist in the production of oral debris leading to disintegration of organic compounds and ultimately producing hydrogen sulfide and methylmercaptan. The known organisms include staphlococci, *B. subtilis*, *B. pyrocaneus*, Colon bacilli, *B. melanogenicus*, Clostridia, *B. sporogenes*, *B. histolyticum*, and *T. mucosum*.

The mouthwash may be delivered as a simple rinse which bathes the tongue. Literature indicates that over 50% of mouth odor originates on the mouth and tongue surface, particularly the posterior dorsal surface of the tongue. Accordingly, a rinse is an effective treatment. However, persons with periodontal involvement may have an increase in oral malodor from disintegrated epithelial cells. A mouth rinse will not penetrate to attack gingival crevicular odorizers. Thus, to optimize treatment with a mouthwash containing chlorine dioxide, the wash must be delivered into the periodontal pockets as well as dorsal and lingual surfaces. To accomplish this, the preferred treatment is achieved by inserting the delivery tip of a syringe into the pockets or gingival crevices or by administering the wash by a mechanically powered water irrigating device such as those of the type sold under the trademark "Water Pik", manufactured by Teledyne Corp. Following irrigation, the user can swish the wash throughout the mouth, covering the dorsal surface of the tongue and other areas.

To improve the taste and appearance of the chlorine dioxide solution, appropriate sweeteners and colorings such as saccharin, peppermint and FTC #3 coloring may be added as is common with commercially available mouthwashes and is well-known to those in the art.

Evaluation of Mouthwash Containing Chlorine Dioxide for its Effect on Volatile Sulfur Compounds The test mouthwash which had a concentration of 0.05%, was dispersed in ⅜ oz. aliquots in individual plastic containers. The study was performed over a 3-hour period on six human subjects with objectionable early morning concentrations of volatile sulfur compounds (VSC) greater than 0.5 ng $CH_3SH$/10 ml mouth air.

Rinsing Procedure: Following initial early morning VSC analysis on the day of evaluation, subjects were instructed to rinse, with vigorous swishing of rinse between teeth, for 30 seconds with ⅜ oz volumes of the test mouthwash. After the rinse was expectorated, the mouth was rinsed for 30 seconds with 15 ml of 18 megavolt pure water.

VSC Analysis: All G.C. analysis were performed in duplicate on each subject at the following times:
1. Initial screening to select subjects with objectionable early morning concentrations of VSC.
2. On the day of evaluation, analysis were performed on early morning mouth air samples before rinsing. These values served as controls. Thus, each subject served as his own control against which the effect of the rinse was calculated. Immediately following these analysis, the subjects rinsed and were re-analyzed, 3 min., 13 min., one hour, two hours and 3 hours post-rinsing. The results are sumarized on the following table:

TABLE 8

SUMMARY MOUTH AIR VSC REDUCTION

| Subject | Early Morning $H_2S$* | $CH_3SH$* | $H_2S$* | One Hour % Red | $CH_2SH$* | % Red | $H_2S$* | Two Hour % Red | $CH_3SH$* | % Red | $H_2S$* | Three Hour % Red | $CH_3SH$* | % Red |
|---|---|---|---|---|---|---|---|---|---|---|---|---|---|---|
| OF. 1 | 0.82 | 0.72 | 0.39 | 52.44 | 0.37 | 48.61 | 0.39 | 52.44 | 0.59 | 18.06 | 0.75 | 8.54 | 1.08 | +50 |
| OF. 2 | 1.30 | 1.04 | 0.29 | 77.69 | 0.17 | 83.65 | 0.41 | 68.46 | 0.24 | 76.92 | 0.45 | 65.38 | 0.23 | 72.88 |
| OF. 3 | 0.98 | 0.77 | 0.77 | 21.43 | 0.57 | 25.97 | 0.69 | 29.59 | 0.52 | 32.47 | 0.82 | 16.33 | 0.62 | 19.48 |
| OF. 4 | 0.73 | 1.04 | 0.39 | 46.58 | 0.2 | 75.00 | 0.37 | 49.32 | 0.31 | 70.19 | 0.47 | 35.62 | 0.46 | 55.76 |
| OF. 5 | 1.56 | 0.88 | 0.58 | 62.82 | 0.41 | 53.41 | 0.75 | 51.92 | 0.40 | 54.55 | 0.86 | 44.87 | 0.80 | 9.09 |
| OF. 6 | 1.12 | 1.41 | 0.40 | 64.29 | 0 | 100 | 0.41 | 63.39 | 0 | 100 | 0.55 | 50.89 | 0.43 | 69.50 |
| Average % Reduction | | | | 54.21 | | 64.44 | | 52.52 | | 58.70 | | 36.94 | | 30.25 |

*ng/10 ml volume of mouth air

The effectiveness of chlorine dioxide was tested both in vivo and in vitro and demonstrated that stabilized chlorine dioxide will kill at the 99% level in ten seconds streptococcus mutans the principle organism implicated in the etiology of dental caries as well as other strains of organisms as demonstrated by the following tests:

IN VITRO
THE BACTERICIDAL EFFECT OF $ClO_2$
AGAINST *STREPTOCOCCUS MUTANS*

| pH of Medium | 200 ppm $ClO_2$ Treatment Seconds | Organisms/0.2 ml | SURVIVED No. Organisms | % Kill |
|---|---|---|---|---|
| 4.80 | 5 | 40,000 | 68 | 99.83 |
| | 10 | 40,000 | 16 | 99.96 |
| | 20 | 40,000 | 5 | 99.99 |
| 5.95 | 5 | 40,000 | 1336 | 99.66 |
| | 10 | 40,000 | 98 | 99.76 |
| | 20 | 40,000 | 101 | 99.75 |
| 5.01 | 5 | 29,600 | *TNTC | 0.0 |
| | 10 | 29,600 | 125 | 99.58 |
| | 20 | 29,600 | 70 | 99.76 |
| 6.06 | 5 | 29,600 | *TNTC | 0.0 |
| | 10 | 29,600 | *TNTC | 0.0 |
| | 20 | 29,600 | 122 | 99.59 |
| 5.06 | 5 | 9,400 | 744 | 92.1 |
| | 10 | 9,400 | 176 | 98.1 |
| | 20 | 9,400 | 44 | 99.5 |
| 6.02 | 5 | 9,400 | 1248 | 86.7 |
| | 10 | 9,400 | 920 | 90.2 |
| | 20 | 9,400 | 640 | 93.2 |

*Too numerous to count.

THE BACTERICIDAL EFFECT OF $ClO_2$
AGAINST *BACTEROIDES GINGIVALIS*

| pH of Medium | 200 ppm $ClO_2$ Treatment Seconds | Organisms/0.2 ml | SURVIVED No. Organisms | % Kill |
|---|---|---|---|---|
| 5.21 | 5 | 53 | 0 | 100 |
| | 10 | 53 | 0 | 100 |
| | 20 | 53 | 0 | 100 |
| 5.96 | 5 | 53 | 0 | 100 |

-continued

THE BACTERICIDAL EFFECT OF ClO$_2$
AGAINST *BACTEROIDES GINGIVALIS*

| pH of Medium | 200 ppm ClO$_2$ | | SURVIVED | |
|---|---|---|---|---|
| | Treatment Seconds | Organisms/0.2 ml | No. Organisms | % Kill |
| | 10 | 53 | 0 | 100 |
| | 20 | 53 | 0 | 100 |

THE BACTERICIDAL EFFECT OF ClO$_2$ AGAINST
*BACTEROIDES MELANINOGENICUS*

| pH of Medium | 200 ppm ClO$_2$ | | SURVIVED | |
|---|---|---|---|---|
| | Treatment Seconds | Organisms/0.2 ml | No. Organisms | % Kill |
| 5.3 | 5 | 100,000 | 100,000 | 0 |
| | 10 | 100,000 | 100,000 | 0 |
| | 20 | 100,000 | 5,000 | 95 |
| 6.15 | 5 | 100,000 | 50,000 | 50 |
| | 10 | 100,000 | 50,000 | 50 |
| | 20 | 100,000 | 0 | 100 |
| 4.97 | 5 | 100,000 | 100,000 | 0 |
| | 10 | 100,000 | 100,000 | 0 |
| | 20 | 100,000 | 3,600 | 97 |
| 5.86 | 5 | 100,000 | 50,000 | 50 |
| | 10 | 100,000 | 50,000 | 50 |
| | 20 | 100,000 | 0 | 100 |
| 4.99 | 10 | 10,000 | 10,000 | 0 |
| | 20 | 10,000 | 0 | 100 |
| | 30 | 10,000 | 0 | 100 |
| 6.29 | 10 | 10,000 | 5,000 | 50 |
| | 20 | 10,000 | 0 | 100 |
| | 30 | 10,000 | 0 | 100 |
| 4.97 | 10 | 10,000 | 10,000 | 0 |
| | 20 | 10,000 | 0 | 100 |
| | 30 | 10,000 | 0 | 100 |
| 5.85 | 10 | 10,000 | 3,000 | 70 |
| | 20 | 10,000 | 0 | 100 |
| | 30 | 10,000 | 0 | 100 |

THE BACTERICIDAL EFFECT OF ClO$_2$ AGAINST
*ACTINOBACILLUS ACTINOMYCETEMCOMITANS*

| pH of Medium | 200 ppm ClO$_2$ | | SURVIVED | |
|---|---|---|---|---|
| | Treatment Seconds | Organisms/0.2 ml | No. Organisms | % Kill |
| 4.97 | 5 | 8,560 | *TNTC | 0 |
| | 10 | 8,560 | 312 | 96.3 |
| | 20 | 8,560 | 67 | 99.2 |
| 5.87 | 5 | 8,560 | *TNTC | 0 |
| | 10 | 8,560 | 2 | 99.9 |
| | 20 | 8,560 | 1 | 99.9 |

*Too numerous to count.

Materials and Methods

Materials used in all experiments:
1.0 AC 5215 Odorid, ClO$_2$ 1000 ppm, Biocide Chemical Co. Norman, OK
1.1 Chlorine-free distilled water employed throughout
1.2 Stirring apparatus, magnetic mixer with magnetic bar; IEC Centrifuge 6000
1.3 Petri plates (12×50 mm, 15×100 mm)
1.4 HCl 0.1N, NaOH 0.1N
1.5 Sodium thiosulfate solution 15%, employed 0.04 ml
1.6 Orthotolidine (o-toluidine) JT Baker, Baker Grade boiling point 200°–201° C.; $C_4 C_6 H_4 HN_2$, Standard Methods for Examination of Water and Wastewater, 14th Ed. 1975 Neutral Orthotolidine Reagent, 0.04 ml employed
1.7 Diluent, saline with 0.5% Tween 80

Materials used in individual experiments:
1.0 Exp. *Streptococcus mutans* ATCC #27152
1.1 Brain Heart Infusion Broth employed for initial culture
1.2 Plate counts performed on plate count agar.
2.0 Exp. *Bacteroides gingivalis* ATCC #33277
2.1 Anaerobic Typtic Soy Agar (TSA) with 5% sheep blood employed for initial isolation.
2.2 Plate counts were performed on anaerobic TSA with 5% horse serum
3.0 Exp. *Bacteroides melaninogenicus* ATCC #15930
3.1 Anaerobic TSA with 5% sheep blood was employed throughout
3.2 Extended time interval for stirring of organisms was 30 seconds
4.0 Exp. *Actinobacillus actinomycetumocomitans* ATCC #29522
4.1 Initial cultures prepared on chocolate agar
4.2 Plate counts were performed on anaerobic TSA without sheep blood

Methods

Initially each ATCC culture employed was grown on the media documented under each organism. After isolation, all cultures were maintained on appropriate media. The initial bacterial count was determined by plating ten-fold serial dilutions of the selected organism in its respective medium. After incubation, the bacterial colonies were counted and 0.2 ml of the selected dilution was employed against ClO$_2$. ClO$_2$ was employed at 200 ppm. 0.8 ml of ClO$_2$ was mixed with 0.2 ml of organisms suspension and map-mixed for the selected length of time in seconds-5, 10, 20, and 30. Two organism-ClO$_2$ mixtures were mixed by a 45° tilting rotation in a small tube for the selected period of time.

In each experiment, subsequent to each mixing time of ClO$_2$ organism-mixtures, excess ClO$_2$ was neutralized by the addition of 0.04 ml of sodium thiosulfate. To assure that complete neutralization of excess ClO$_2$ had occurred, 0.04 orthotolidine was added to each ClO$_2$-organism-sodium thiosulfate mixture. When ClO$_2$ is neutralized, the mixture remains clear. If residual ClO$_2$ is present, the mixture turns yellow after the addition of orthotolidine. Additional controls to determine the effect of each reagent singly or in combination against each organism include sodium thiosulfate-organism mixtures and sodium thiosulfate orthotolidine organism mixtures. A control plate count without reagents was included for each organism.

All cultures except *Streptococcus mutans* were grown anaerobically in CO at 37° C. for 48-96 hours. *Streptococcus mutans* was grown aerobically at 37° C. for 48 hours.

In Vivo Chlorine Dioxide Evaluation

Thirty-nine periodontal pockets in twenty-nine patients were examined by dark field and phase microscopy. The motility and density of bacteria were evaluated from zero to three with zero being no activity and three very active.

Of the thirty-nine teeth, thirty were molars, three were bicuspids and six were in the anterior region. Pocket dept ranged from 4 to 12 millimeters.

The patients were instructed to use a 0.1% chlorine dioxide solution twice daily. Four of the patients used chlorine dioxide as a mouth rinse and twenty-five used it as an irrigant with monoject 412 twelve cc syringe. The findings follow:

| CLINICAL EFFECT OF .1% CHLORINE DIOXIDE ||||||||
|---|---|---|---|---|---|---|---|
| TOOTH # | CODE # | SURFACE | BEFORE PHASE | AFTER PHASE | % CHANGE | BEFORE DARK FIELD | BEFORE DARK FIELD | % CHANGE |
| 14 | 001 | M | 2 | 0 | 100% | 3 | 1+ | 50% |
| 23 | 001 | D | + | 0 | 100% | 2 | + | 75% |
| 30 | 002 | D | 0 | 0 | 0% | 1 | 0 | 100% |
| 18 | 003 | D | 2 | 0 | 100% | 2+ | 1− | 70% |
| 15 | 004 | L | + | 0 | 100% | + | + | 0% |
| 18 | 004 | D | 2 | 0 | 100% | 2+ | 1 | 60% |
| 14 | 005 | M | 2 | 1 | 50% | 2 | 2 | 0% |
| 30 | 005 | L | 1 | 0 | 100% | 2 | 0 | 100% |
| 15 | 006 | L | 0 | 0 | 0 | 2 | 0 | 100% |
| 19 | 007 | D | 0 | 0 | 0 | 3 | 0 | 100% |
| 31 | 008 | B | 2 | 0 | 100% | 2+ | 0 | 100% |
| 7 | 009 | D | 3 | 0 | 100% | 3 | 2 | 33% |
| 2 | 010 | M | 1 | 0 | 100% | 2 | 0 | 100% |
| 4 | 011 | M | 0 | 0 | 0 | 2 | 0 | 100% |
| 15 | 011 | D | 1 | 0 | 100% | 3 | 1− | 75% |
| 3 | 012 | M | 2 | 1− | 63% | 3 | 2 | 33% |
| 14 | 012 | M | 2 | 1 | 50% | 3 | 2 | 33% |
| 18 | 013 | M | 0 | 0 | 0 | 3 | 1 | 67% |
| 3 | 014 | M | 0 | 0 | 0 | 1 | 0 | 100% |
| 2 | 015 | M | 2 | 1 | 50% | 3 | 2 | 33% |
| 2 | 015 | D | 2 | + | 75% | 3 | + | 83% |
| 21 | 016 | D | 0 | 0 | 0 | 2+ | 0 | 100% |
| 14 | 017 | M | 1 | 0 | 100% | 3 | 2 | 33% |
| 3 | 018 | M | 1 | 0 | 100% | 1 | 0 | 100% |
| 32 | 019 | D | 1+ | 0 | 100% | 2 | 0 | 100% |
| 31 | 020 | B | 2 | + | 75% | 3 | + | 83% |
| 2 | 021 | M | 2+ | 1 | 60% | 3 | 2 | 33% |
| 32 | 022 | D | 1 | 0 | 100% | 1 | + | 50% |
| 31 | 023 | M | 1 | 0 | 100% | 3 | 0 | 100% |
| 3 | 024 | D | 2 | 0 | 100% | 2 | 0 | 100% |
| 15 | 025 | D | 2 | 0 | 100% | 3 | 1 | 67% |
| 26 | 025 | D | 0 | 0 | 0 | 3 | 1 | 67% |
| 4 | 026 | M | 2 | 0 | 100% | 2+ | 1− | 70% |
| 12 | 026 | M | 1 | + | 50% | 3 | + | 83% |
| 8 | 027 | B | 1 | 0 | 100% | 2 | 1 | 50% |
| 3 | 028 | M | 1 | 0 | 100% | 3 | 1 | 67% |
| 31 | 029 | M | 1 | + | 50% | 3 | 1+ | 50% |
| 11 | 030 | D | + | 0 | 100+ | 1 | + | 50% |

| EVALUATION DATA |||
|---|---|---|
| Number of Pockets | % Resolution | % of Total |
| Phase (Thirty Pockets with Activity) |||
| 21 | 100% | 70% |
| 2 | 75% | 6.67% |
| 1 | 63% | 3.33% |
| 1 | 60% | 3.33% |
| 5 | 50% | 16.07% |
| Mean resolution |||
| (All bacterial activity stopped or was reduced). |||
| Dark Field (Thirty-nine pockets with Activity) |||
| 14 | 100% | 35.89% |
| 3 | 83% | 7.69% |
| 2 | 75% | 5.13% |
| 2 | 70% | 5.13% |
| 4 | 67% | 10.26% |
| 1 | 60% | 2.56% |
| 5 | 50% | 12.82% |
| 6 | 33% | 15.38% |
| (Two of the pockets exhibited no reduction in bacteria after the use of Chlorine Dioxide.) |||

EXAMPLE II

Toothpaste

As demonstrated above, chlorine dioxide can be an effective agent on odor producing microorganisms and enzymes. However, the effectiveness of chlorine dioxide can be enhanced when included as an ingredient of a toothpaste. Toothpaste is more effective than a rinse for removing malodor from the gums or gingiva. The action of the brush dislodges dead cells and putrescent debris from the gingival crevices as well as on the various mouth surfaces and on the tongue. The chlorine dioxide contained in the toothpaste acts as discussed above to prevent malodor and serve as a deodorizer by attacking hydrogen sulfide and methylmercaptan. A typical toothpaste would have the following composition: Chlorine dioxide approximately 0.005% to 0.2%, detergent polishing agent; calcium carbonate; flavoring, saccharin; peppermint; coloring agent. These other ingredients may vary and are the basic ingredients in many toothpastes as is well-known to those in the art. Other formulations including chlorine dioxide as the active incredient would work as well.

EXAMPLE III

Anti-Plaque Agent

Dental plaque, as mentioned above, is formed by a combination of actions beginning with saliva coating the the tooth and a subsequent adhesion to the coating by streptococcus bacterial forms. *S. mutans* degrade sucrose into glucose or fructose which are then compounded into dextrans and levans. The dextrans act as a nutrient substrate for the growth of additional organisms and the production of acids which demineralize tooth enamel and dentin causing tooth decay. As indicated in the test data above, chlorine dioxide is lethal to *Streptococcus mutans* in vitro and materally reduces their numbers in vivo. Dental plaque formation is reduced when the microbial content of the mouth is reduced. Thus, chlorine dioxide is an effective anitmicrobial agent which functions as a dental plaque retardant or preventative and as an anti-cariogenic agent. Preferred concentrations are in the range from 0.005% to 0.2% in solutions as for example, in de-ionized water with suitable coloring and flavorings for patient comfort.

EXAMPLE IV

Anti-Gingivitis, Anti-Periodontitis and Gingival Bleeding Preventative

Gingivitis and the various forms of periodontitis are known to be caused by bacteria. Principal forms implicated are *Bacteroides gingivalis* and *Actinobacillus actionmycetumcomitans*. *Gingivitis occurs from coronal dental plaque and periodontitis by the infection extending into the periodontal pockets or spaced between the gingiva (gums) and the tooth root. Thus control of gingivitis is by reduction of microorganisms in the coronal dental plaque and control of periodontitis by reduction of pocket bacterial plaque in the gingival crevices as well as the saliva.*

Clinical evidence has documented improvement in treatment of the above diseases when stabilized chlorine dioxide is used. The organisms currently implicated in the above are listed as follows:
1. Gingivitis
    Actinomyces forms including *Actinomyces israeli*
    *coccus* forms
2. Acute Necrotizing Ulcerative Gingivitis
    *spirochetes*
    *Bacteroides intermedius*
    *Fusiform nucleatum*
3. Juvenile Periodontitis
    *Actinobacillus actinomycetumcomitans*
    *capnocytophagia*
    *Bacteroides intermedius*
4. Adult periodontitis
    *Bacteroides gingivalis*
    *Bacteroides intermidius*
    *Actinobacillus actinomycetumcomitans*
    *Vibrio nucleatum*
    *Fusobactium nucleatum*
    *Fusobactium bacteroides*
    Anerobic cocci Research has demonstrated that stabilized chlorine dioxide is lethal to *Bacteriodes gingivalis* and *Actincbacillus actinomycetumcomitans* in vitro at the 95% level in twenty seconds with a 0.02% concentration. Research in vivo demonstrates that these organisms are significantly reduced or eliminated in humans when chlorine dioxide agent is applied to the pocket area using a syringe or water injection device with a needle to force penetration into the gingival crevices with the chlorine dioxide concentration in the range of 0.05% to 0.2%. Both gingivitis and periodontitis cause an increase in the rate of epithelial cells sloughing aggrevating oral malodor and causing some ulceration of tissue leaving the gingival bleeding which is also reduced by treatment with a solution of stabilized chlorine dioxide.

Chlorine dioxide is thus highly useful in the treatment of gingivitis, periodontitis in its various forms and bleeding gingiva.

EXAMPLE V

Denture Soak

The malodors of the mouth result substantially from the volatile sulfur compounds which are present in saliva. Saliva coats and penetrates dental prosthetic devices including full dentures and partial dentures. Further, food and other cellular debris adheres to dental prostheses. Bacteria accumulates on and in the microscopic faults and pores of these prosthetic devices. Chlorine dioxide has been demonstrated as a bactericide and disinfectant and is effective for neutralizing sulfur-based malodors, removing organic debris from dental prosthesis and as a disinfectant and bactericide. As a dental soak the solution is antimicrobial, removes sulfur compounds and breaks down organic material and can be used in solution form having a concentration of from approximately 0.002% to 0.27%.

EXAMPLE VI

Cellular Debridement Agent

Many wounds and desquamative diseases such as *Lichen planus, Desquamative gingivitis* and desquamative dermatological disease are aided by organic debridement agents and antibicrobial agents. Solution or composition containing chlorine dioxide in 0.05% to 0.1% and higher concentrations is effective to treat these problems. One particular application would be in veterinarian applications for the purpose of reducing odor attendant to these wounds and diseases.

EXAMPLE VII cl Sanitizer and Cold Sterilization Agent

The known bacterial, fungicidal and viralcidal characteristics of chlorine dioxide also make it extremely useful as a sanitizer which can be a solution in which materials can be dipped or by application in an areosol spray. The sanitizer can be used for food, sickroom use, bathroom and cold sterilization of many instruments and pieces of equipment are generally not amenable to autoclave sterilization. Again, the concentration of the sanitizing or sterilization agent would preferably be in the range of from 0.005% to 2.0%.

EXAMPLE VIII

Contact Lens Soak

Contact lenses accumulate bacteria and cellular debris from the eye. The known bactericidal, fungicidal and viraloidal capacity of chlorine dioxide along with the low toxicity makes chlorine dioxide solution an ideal lens soak. In addition, capacity to degrade organic debris keeps the lens clean and nonirritating. The preferred range of concentration is 0.005% to 0.2% in sterilized water.

It will be seen from the foregoing that chlorine dioxide in solution or as part of a composition or compound is effective in treating and preventing the formation of mouth malodor, as a suitable chemical plaque control agent, and as a bactericide, viralcide and fungicide superior to other compositions used today. Chlorine dioxide has been used for many years in other areas and extensive study in animals and in man have demonstrated its low toxicity and safety. Chlorine dioxide is approved by the Environmental Protection Agency (EPA Reg. No. 9048-3) for water purification, food preparation and preservation as well as a bacteriostatic, fungistatic and viralstatic agent.

It will be obvious that various changes, alterations and modifications to the method and process described herein may be made. To the extent that such changes, alterations and modifications do not depart from the spirit and scope of the appended claims, they are intended to be emcompassed therein.

I claim:

1. A method for reducing dental plaque, said method comprising the step of retarding degradation of sucrose into glucose or fructose by killing and by reducing the number of streptococcus mutans to a more than 90% level through topical application within the oral cavity for a period of ten seconds of a solution containing stabilized chlorine dioxide in a concentration in the range of 0.005% to 0.2%.

2. A method for reducing dental plaque by altering the milieu of the ecology of the bacteria within the oral cavity, said method comprising the steps of:
   (a) applying within the oral cavity for a period of ten seconds, a solution containing stabilized chlorine dioxide in a concentration of 0.005% to 0.2%;
   (b) retarding formation of dextrans and levans; and
   (c) interfering with the supply of nutrition to the bacteria;
whereby, the milieu of the bacteria within the oral cavity is altered.

3. A method for reducing dental plaque by altering the milieu of the ecology of the bacteria within the oral cavity, said method comprising the steps of:
   (a) applying within the oral cavity for a period of ten seconds a solution containing stabilized chlorine dioxide in a concentration; in the range of 0.005% to 0.2%;
   (b) breaking down the double bonds in the glucosyltransferases present in the oral cavity;
   (c) preventing degradation of sucrose into glucose and fructose; and
   (d) preventing formulation of dextrans, glucans, lucans and fructans; whereby, the resulting interference with the supply of nutrition to the bacteria present within the oral cavity reduces the formation of dental plaque.

4. The method as set forth in claim 2 wherein said step of retarding includes the step of killing and reducing the number of streptococcus mutans to a greater than 90% level.

* * * * *